(12) United States Patent
Liu et al.

(10) Patent No.: US 10,881,356 B2
(45) Date of Patent: Jan. 5, 2021

(54) MOOD MONITORING DEVICE, SYSTEM AND METHOD

(71) Applicant: BOE Technology Group Co., Ltd., Beijing (CN)

(72) Inventors: Zijun Liu, Beijing (CN); Honglei Zhang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 16/023,662

(22) Filed: Jun. 29, 2018

(65) Prior Publication Data

US 2019/0053770 A1    Feb. 21, 2019

(30) Foreign Application Priority Data

Aug. 17, 2017    (CN) .......................... 2017 1 0708104

(51) Int. Cl.
*G08B 23/00*    (2006.01)
*A61B 5/00*    (2006.01)
(Continued)

(52) U.S. Cl.
CPC ............ *A61B 5/746* (2013.01); *A61B 5/0476* (2013.01); *A61B 5/165* (2013.01); *A61B 5/0482* (2013.01); *A61B 5/741* (2013.01); *A61B 5/742* (2013.01)

(58) Field of Classification Search
CPC ....... A61B 5/746; A61B 5/0476; A61B 5/165; A61B 5/742; A61B 5/741; A61B 5/0482; A61B 5/0077; A61B 5/7267; A61B 5/7246; A61B 5/0261; A61B 5/0295; A61B 5/02055; A61B 5/1176; A61B 5/441;
(Continued)

(56) References Cited

U.S. PATENT DOCUMENTS

2014/0221866 A1    8/2014    Quy
2015/0334808 A1*   11/2015   Hack ..................... A61M 21/00
                                                        315/297
(Continued)

FOREIGN PATENT DOCUMENTS

CN    102300163 A    12/2011
CN    202505349 U    10/2012
(Continued)

OTHER PUBLICATIONS

First office action of Chinese application No. 201710708104.1 dated Oct. 9, 2019.
(Continued)

*Primary Examiner* — Anh V La
(74) *Attorney, Agent, or Firm* — Fay Sharpe LLP (57) ABSTRACT

A mood monitoring device, system and method are provided. The mood monitoring device includes one or more processors; and a storage. The storage stores one or more programs which are configured to be executed by the one or plurality of processors. The one or more programs comprise instructions for performing the following operations: receiving a status message that is sent by a terminal and indicates a mood status of a user, the terminal and the mood monitoring device having a binding relationship; and presenting a message that reflects the mood status of the user in accordance with the status message.

20 Claims, 5 Drawing Sheets

(51) Int. Cl.
    *A61B 5/16*           (2006.01)
    *A61B 5/0476*       (2006.01)
    *A61B 5/0482*       (2006.01)

(58) Field of Classification Search
    CPC .... A61B 5/02405; G16H 50/20; G16H 20/70;
                                              G16H 30/40
    USPC ..... 340/573.1, 573.4, 539.1, 539.11, 539.12,
                                                       340/539.15
    See application file for complete search history.

(56) References Cited

U.S. PATENT DOCUMENTS

| | | | | |
|---|---|---|---|---|
| 2016/0140320 | A1* | 5/2016 | Moturu | G06F 19/3481 |
| | | | | 434/236 |
| 2017/0042439 | A1* | 2/2017 | Yeow | G16H 10/60 |
| 2017/0238859 | A1* | 8/2017 | Sadowsky | G06F 16/24 |
| 2017/0352283 | A1* | 12/2017 | Lau | G09B 5/06 |

FOREIGN PATENT DOCUMENTS

| | | | |
|---|---|---|---|
| CN | 103654798 A | 3/2014 | |
| CN | 103690165 A | 4/2014 | |
| CN | 106580260 A | 4/2017 | |

OTHER PUBLICATIONS

Third office action of Chinese application No. 201710708104.1 dated Aug. 28, 2020.

* cited by examiner

MOOD MONITORING DEVICE, SYSTEM AND METHOD

This application claims priority to Chinese Patent Application No. 201710708104.1, filed with the State Intellectual Property Office on Aug. 17, 2017 and titled "Mood Monitoring Device and System", the entire contents of which are incorporated herein by reference.

TECHNICAL FIELD

The present disclosure relates to a mood monitoring device, system and method.

BACKGROUND

With the rapid development of the network technology, terminals (for example, mobile terminals) have become more and more popular. As a mood monitoring device, a terminal can make the users in different places know the mood of another user by means of voice speed, intonation, facial expression, body movement, etc., thus improving the relationship between the users. For example, any of the multiple users who are making a video chat via the terminal may know the mood of another user during the video chat.

However, sometimes, the users may not express their own real mood through voice speed, intonation, facial expression or body movement such that the terminal fails to help the users accurately know the mood of another user. Hence, as the mood monitoring device, the terminal is relatively poorer in mood monitoring flexibility and reliability.

SUMMARY

Embodiments of the present disclosure provide a mood monitoring device, system and method.

In a first aspect, there is provided a mood monitoring device, comprising: one or a plurality of processors; and a storage, wherein the storage stores one or a plurality of programs, which are configured to be executed by the one or plurality of processors and comprises instructions for performing the following operations: receiving a status message that is sent by a terminal and indicates a mood status of a user, the terminal and the mood monitoring device having a binding relationship; and presenting a message that reflects the mood status of the user in accordance with the status message.

Optionally, the mood monitoring device comprises a light-emitting diode (LED), wherein the one or plurality of programs further comprises instructions for performing the following operation: adjusting a light-emitting status parameter of the LED in accordance with the status message such that a light-emitting status of the LED corresponds to the mood status of the user, wherein the light-emitting status parameter comprises at least one of a color, a brightness and a flash mode.

Optionally, the one or plurality of programs further comprises instructions for performing the following operations: inquiring a corresponding relationship between a preset mood status and the light-emitting status parameter; acquiring a target light-emitting status parameter that corresponds to the mood status indicated by the status message when the corresponding relationship has recorded the mood status indicated by the status message; and adjusting the light-emitting status parameter of the LED into the target light-emitting status parameter.

Optionally, the LED comprises a red LED, a green LED and a blue LED, and the one or plurality of programs further comprises instructions for performing the following operation: controlling the number and the current of light-emitting LEDs in each color in the LEDs in accordance with the status message to adjust the light-emitting status parameter of the LEDs.

Optionally, the one or plurality of programs further comprises instructions for performing the following operation: giving a voice prompt in accordance with the status message such that the voice prompt corresponds to the mood status of the user.

Optionally, the one or plurality of programs further comprises instructions for performing the following operation: sending a pushing message that indicates the mood status of the user to another terminal which has a binding relationship with the mood monitoring device.

Optionally, the mood monitoring device is a mobile terminal.

In a second aspect, there is provided a mood monitoring device, comprising: one or a plurality of processors; and a storage, wherein the storage stores one or a plurality of programs, which are configured to be executed by the one or plurality of processors and comprises instructions for performing the following operations: monitoring an electroencephalography (EEG) signal of a user, determining a mood status of the user in accordance with the EEG signal, and generating a status message that indicates the mood status of the user; and sending the status message that indicates the mood status of the user to a terminal which has a binding relationship with the mood monitoring device.

Optionally, the one or plurality of programs further comprises instructions for the following operations: acquiring a frequency band of the EEG signal of the user; inquiring a corresponding relationship between a preset frequency band and the mood status; acquiring a target mood status that corresponds to the frequency band of the EEG signal of the user when the corresponding relationship has recorded the frequency band of the EEG signal of the user; and determining the target mood status as the mood status of the user.

Optionally, the one or plurality of programs further comprises instructions for performing the following operation: providing a reference message in accordance with the mood status of the user, the reference message being used to prompt the user to adjust his/her mood status.

Optionally, the mood monitoring device is a mobile terminal.

In a third aspect, there is provided a mood monitoring system, comprising a first terminal and a second terminal, wherein the second terminal comprises the mood monitoring device in the first aspect; and the first terminal is configured to monitor an electroencephalography (EEG) signal of a user, to determine a mood status of the user in accordance with the EEG signal, to generate a status message that indicates the mood status of the user, and to send the status message that indicates the mood status of the user to the second terminal which has a binding relationship with the first terminal.

In a fourth aspect, there is provided a mood monitoring method, comprising: monitoring an electroencephalography (EEG) signal of a user, determining a mood status of the user in accordance with the EEG signal, and generating a status message that indicates the mood status of the user, by means of a first terminal; sending the status message that indicates the mood status of the user to a second terminal which has a binding relationship with the first terminal, by means of the first terminal; and presenting a message that reflects the mood status of the user by means of the second terminal in accordance with the status message.

Optionally, determining the mood status of the user in accordance with the EEG signal by means of the first terminal comprises: acquiring a frequency band of the EEG signal of the user by means of the first terminal; inquiring a corresponding relationship between a preset frequency band and the mood status by means of the first terminal; acquiring a target mood status that corresponds to the frequency band of the EEG signal of the user by means of the first terminal when the corresponding relationship between the preset frequency band and the mood status has recorded the frequency band of the EEG signal of the user; and determining the target mood status as the mood status of the user by means of the first terminal.

Optionally, after determining the mood status of the user in accordance with the EEG signal, the method further comprises: providing a reference message by means of the first terminal in accordance with the mood status of the user, the reference message being used to prompt the user to adjust his/her mood status.

Optionally, the second terminal comprises a light-emitting diode (LED), and said presenting the message that reflects the mood status of the user by means of the second terminal in accordance with the status message comprises: adjusting a light-emitting status parameter of the LED by means of the second terminal in accordance with the status message such that a light-emitting status of the LED corresponds to the mood status of the user, wherein the light-emitting status parameter comprises at least one of a color, a brightness and a flash mode.

Optionally, adjusting the light-emitting status parameter of the LED by means of the second terminal in accordance with the status message comprises: inquiring a corresponding relationship between a preset mood status and the light-emitting status parameter by means of the second terminal; acquiring a target light-emitting status parameter that corresponds to the mood status indicated by the status message, by means of the second terminal when the corresponding relationship between the preset mood status and the light-emitting status parameter has recorded the mood status indicated by the status message; and adjusting the light-emitting status parameter of the LED into the target light-emitting status parameter by means of the second terminal.

Optionally, the LED comprises a red LED, a green LED and a blue LED, and adjusting the light-emitting status parameter of the LED by means of the second terminal in accordance with the status message comprises: controlling the number and the current of light-emitting LEDs in each color in the LEDs by means of the second terminal in accordance with the status message to adjust the light-emitting status parameter of the LEDs.

Optionally, after sending the status message that indicates the mood status of the user to the second terminal by means of the first terminal, the method further comprises: giving a voice prompt by means of the second terminal in accordance with the status message such that the voice prompt corresponds to the mood status of the user.

Optionally, after sending the status message that indicates the mood status of the user to the second terminal by means of the first terminal, the method further comprises: sending a pushing message that indicates the mood status of the user to a third terminal which has a binding relationship with the second terminal, by means of the second terminal.

In a fifth aspect, there is provided a mood monitoring method applied to a second terminal, comprising: receiving a status message that is sent by a first terminal and indicates a mood status of a user, the first terminal and the second terminal having a binding relationship; and presenting a message that reflects the mood status of the user in accordance with the status message.

Optionally, the second terminal comprises a light-emitting diode (LED), and presenting a message that reflects the mood status of the user in accordance with the status message comprises: adjusting a light-emitting status parameter of the LED in accordance with the status message such that a light-emitting status of the LED corresponds to the mood status of the user, the light-emitting status parameter comprising at least one of a color, a brightness and a flash mode.

Optionally, adjusting the light-emitting status parameter of the LED in accordance with the status message comprises: inquiring a corresponding relationship between a preset mood status and the light-emitting status parameter; acquiring a target light-emitting status parameter that corresponds to the mood status indicated by the status message, when the corresponding relationship has recorded the mood status indicated by the status message; and adjusting the light-emitting status parameter of the LED into the target light-emitting status parameter.

Optionally, the LED comprises a red LED, a green LED and a blue LED, and adjusting the light-emitting status parameter of the LED in accordance with the status message comprises: controlling the number and the current of light-emitting LEDs in each color in the LEDs in accordance with the status message to adjust the light-emitting status parameter of the LEDs.

Optionally, after receiving the status message that is sent by the first terminal and indicates a mood status of a user, the method further comprises: giving a voice prompt in accordance with the status message such that the voice prompt corresponds to the mood status of the user.

Optionally, after receiving the status message that is sent by the first terminal and indicates a mood status of a user, the method further comprises: sending a pushing message that indicates the mood status of the user to a third terminal which has a binding relationship with the second terminal.

In a sixth aspect, there is provided a mood monitoring method applied to a first terminal, comprising: monitoring an electroencephalography (EEG) signal of a user, determining a mood status of the user in accordance with the EEG signal, and generating a status message that indicates the mood status of the user; and sending the status message that indicates the mood status of the user to a second terminal which has a binding relationship with the first terminal.

Optionally, said determining a mood status of the user in accordance with the EEG signal comprises: acquiring a frequency band of the EEG signal of the user; inquiring a corresponding relationship between a preset frequency band and the mood status; acquiring a target mood status that corresponds to the frequency band of the EEG signal of the user when the corresponding relationship has recorded the frequency band of the EEG signal of the user; and determining the target mood status as the mood status of the user.

Optionally, after determining the mood status of the user in accordance with the EEG signal, the method further comprises: providing a reference message in accordance with the mood status of the user, the reference message being used prompt the user to adjust his/her mood status.

In a seventh aspect, there is provided a computer-readable storage medium including instructions stored therein. The computer-readable storage medium, when operating in a computer, causes the computer to implement the mood monitoring method provided in the fifth aspect.

In an eighth aspect, there is provided a computer program product including instructions. The computer program product, when operating in a computer, causes the computer to implement the mood monitoring method provided in the fifth aspect.

In a ninth aspect, there is provided a computer-readable storage medium including instructions stored therein. The computer-readable storage medium, when operating in a computer, causes the computer to implement the mood monitoring method provided in the sixth aspect.

In a tenth aspect, there is provided a computer program product including instructions. The computer program product, when operating in a computer, causes the computer to implement the mood monitoring method provided in the sixth aspect.

DETAILED DESCRIPTION

To make principles and advantages of the present disclosure clearer, the embodiments of the present disclosure will be further described in detail below in conjunction with the accompanying drawings.

Figure 1:
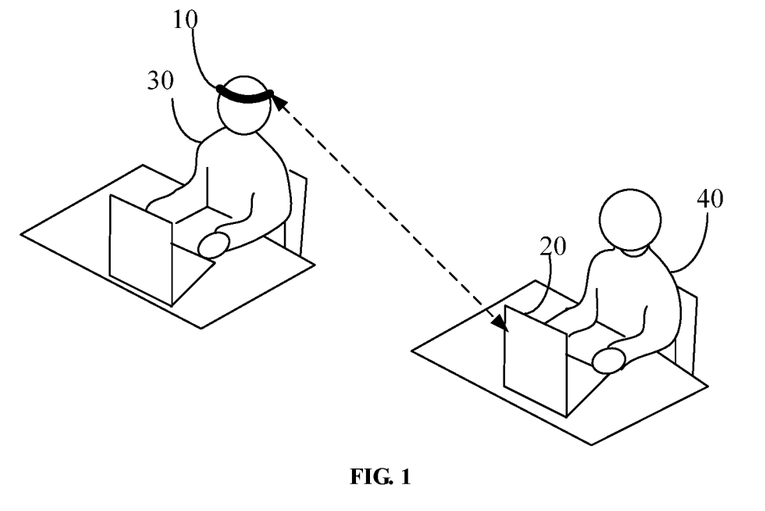
FIG. 1 is a diagram of an implementation environment involved in various embodiments of the present disclosure.

FIG. 1 illustrates a schematic view of an implementation environment involved in various embodiments of the present disclosure. The implementation environment may comprise a first terminal 10 and a second terminal 20 which have a binding relationship. A user who uses the first terminal 10 is a first user 30 while a user who uses the second terminal 20 is a second user 40. The first terminal 10 acquires a mood status of the first user 30 and sends a status message that indicates the mood status of the first user 30 to the second terminal 20. The second terminal 20 presents a message that reflects the mood status of the first user 30 in accordance with the status message that is sent by the first terminal 10. Exemplarily, the mood status may be a sad status, a relaxed status, a tension status or the like. The second terminal 20 may give out light in a corresponding color or give a corresponding voice prompt or the like, such that the second user 40 may know a mood of the first user 30 in time. In this implementation environment, relatives and friends in different places may know the mood of each other in real time, which facilitates enhancement of their mood exchange.

Figure 2:
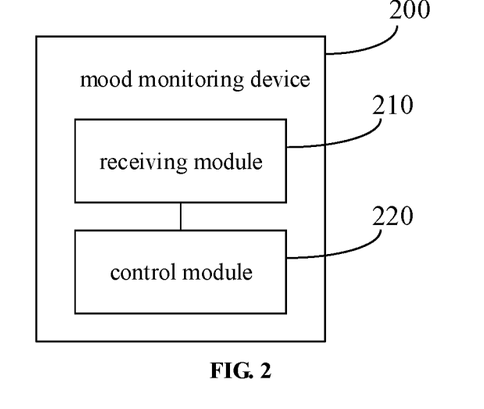
FIG. 2 is a structural diagram of a mood monitoring device provided in an embodiment of the present disclosure.

FIG. 2 illustrates a structural schematic view of a mood monitoring device provided by an embodiment of the present disclosure. The mood monitoring device may be applied to the second terminal 20 in the implementation environment shown in FIG. 1. Referring FIG. 2, the mood monitoring device 200 comprises a receiving module 210 and a control module 220.

The receiving module 210 is configured to receive a status message, which is sent by a terminal and indicates a mood status of a user. The terminal and the mood monitoring device have a binding relationship. Exemplarily, the terminal may be the first terminal 10 in the implementation environment shown in FIG. 1. The user is the first user 30 who uses the first terminal 10. That is, the receiving module of the second terminal is configured to receive the status message, which is sent by the first terminal and indicates the mood status of the first user.

Exemplarily, the user who uses the first terminal is the first user while the user who uses the second terminal is the second user. For example, when the first user is a communication friend of the second user and the second user acquires the mood status of the first user by means of the second terminal, the second terminal of the second user may receive the status message, which is sent by the first terminal and indicates the mood status of the first user.

The control module 220 is configured to present a message that reflects the mood status of the user in accordance with the status message.

To sum up, in the mood monitoring device provided by the embodiment of the present disclosure, the receiving module receives the status message, which is sent by the terminal and indicates the mood status of the user. The control module may present the message that reflects the mood status of the user in accordance with the status message. Compared with the prior art, the mood monitoring device provided by the embodiment of the present disclosure may help the user know the mood of another user, thus enhancing a mood exchange between relatives and friends in different places and improving the flexibility and reliability in mood monitoring.

Figure 3:
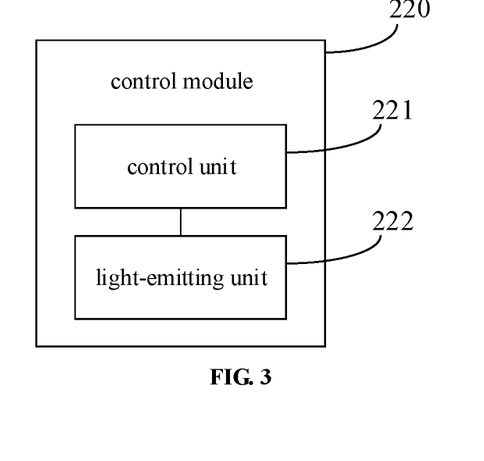
FIG. 3 is a structural diagram of a control module provided in an embodiment of the present disclosure.

Optionally, as shown in FIG. 3, the control module 220 comprises a control unit 221 and a light-emitting unit 222.

The control unit 221 is configured to adjust a light-emitting status parameter of the light-emitting unit 222 in accordance with a status message such that a light-emitting status of the light-emitting unit 222 corresponds to a mood status of a user. The light-emitting status parameter comprises at least one of a color, a brightness and a flash mode.

Optionally, the control unit 221 is configured to: inquire a corresponding relationship between a preset mood status and the light-emitting status parameter; acquire a target light-emitting status parameter that corresponds to the mood status indicated by the status message when the corresponding relationship has recorded the mood status indicated by the status message; and adjust the light-emitting status parameter of the light-emitting unit 222 into the target light-emitting status parameter.

Exemplarily, the corresponding relationship between the preset mood status and the light-emitting status parameter may be as shown in Table 1. Exemplarily, the light-emitting status parameter is orange light or red light when the mood status is a sad status; the light-emitting status parameter is yellow light when the mood status is a relaxed status; and the light-emitting status parameter is blue light or green light when the mood status is a tension status. Exemplarily, when the mood status, indicated by the status message which is sent by the first terminal and indicates the mood status of the first user, is the relaxed status, the control unit inquires Table 1 to acquire the target light-emitting status parameter (yellow light) that corresponds to the relaxed status. Then, the control unit adjusts light emitted by the light-emitting unit to be yellow.

TABLE 1

| Mood status | light-emitting Status Parameter |
| --- | --- |
| Sad status | Orange light or red light |
| Relaxed status | Yellow light |
| Tension status | Blue light or green light |

Optionally, the light-emitting unit 222 comprises a red light-emitting diode (LED), a green LED and a blue LED. The control unit 221 is configured to control the number and the current of light-emitting LEDs in each color in the light-emitting unit 222 in accordance with the status message to adjust the light-emitting status parameter of the light-emitting unit 222. For example, the control unit controls the number and the current of light-emitting LEDs such that the light-emitting unit emits flashing yellow light. The light-emitting status parameter that corresponds to the mood status may be set in advance by the second user.

Figure 4:
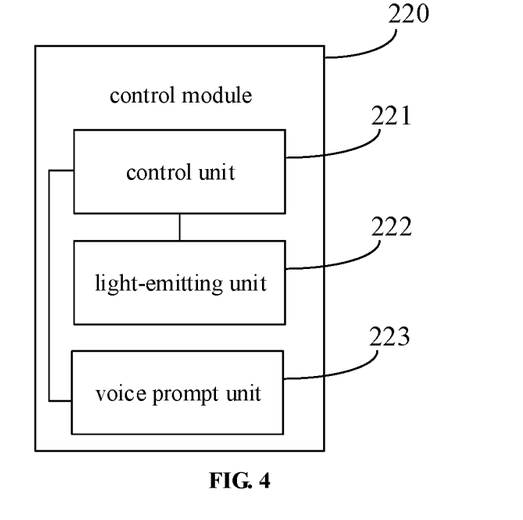
FIG. 4 is a structural diagram of another control module provided in an embodiment of the present disclosure.

Furthermore, FIG. 4 is a structural schematic view of another control module provided by an embodiment of the present disclosure on the basis of FIG. 3. As shown in FIG. 4, the control module 220 further comprises a voice prompt unit 223.

The control unit 221 is further configured to control the voice prompt unit 223 to give a voice prompt in accordance with the status message such that the voice prompt corresponds to the mood status of the user.

In the embodiment of the present disclosure, the control unit may further control the voice prompt unit to give a corresponding voice prompt in accordance with a control message. Table 2 exemplarily shows three corresponding relationships between the voice prompt and the mood statuses. Exemplarily, the voice prompt is T1 when the mood status is a sad status, and for example, T1 may be a classical song; the voice prompt is T2 when the mood status is a relaxed status, and for example, T2 may be a popular song; and the voice prompt is T3 when the mood status is a tension status, and for example, T3 is may be piano music. Exemplarily, the first terminal sends the status message that indicates the mood status of the first user. When the mood status indicated by the status message is the relaxed status, the control unit controls the voice prompt unit to play the popular song. The control unit may also control the voice prompt unit to give other voice prompts. The voice prompt that corresponds to the mood status may be set by the second user in advance.

TABLE 2

| Mood status | Voice Prompt |
| --- | --- |
| Sad status | T1 |
| Relaxed status | T2 |
| Tension status | T3 |

Exemplarily, the mood monitoring device provided by the embodiment of the present disclosure may be a mobile terminal. Exemplarily, the mobile terminal may be a mobile phone with an earphone hole. The control module may be realized by a hardware structure and may be plugged into the earphone hole of the mobile phone. In addition, the control module may also be realized through an application program.

Furthermore, the mood monitoring device may further comprise a monitoring module and a sending module. The monitoring module is configured to monitor an EEG signal, to determine the mood status of the user in accordance with the EEG signal of the user, and to generate the status message that indicates the mood status of the user. The sending module is configured to send the status message that indicates the mood status of the user to a terminal. The user is the second user in the implementation environment shown in FIG. 1. The terminal is the first terminal in the implementation environment shown in FIG. 1. That is, the sending module of the mood monitoring device may send the status message that indicates the mood status of the second user to the first terminal.

Optionally, the monitoring module may comprise a monitoring unit and an analyzing unit. The monitoring unit is configured to monitor an EEG signal of a user and to send the EEG signal of the user to the analyzing unit. The analyzing unit is configured to determine a mood status of the user in accordance with the EEG signal of the user and to generate a status message that indicates the mood status of the user.

Optionally, the analyzing unit is configured to acquire a frequency band of the EEG signal of the user, to inquire a corresponding relationship between a preset frequency band and the mood status, to acquire a target mood status that corresponds to the frequency band of the EEG signal of the user when the corresponding relationship has recorded the frequency band of the EEG signal of the user, and to determine the target mood status as the mood status of the user.

Optionally, the mood monitoring device may further provide a reference message in accordance with the mood status of the user. The reference message is used to prompt the user to adjust his/her mood status. The user is the second user.

Furthermore, supposing that the mood monitoring device is a mobile terminal, the mobile terminal may be equipped with an application program configured to manage the mood status of the user. Exemplarily, the mobile terminal sends a pushing message to another mobile terminal which has a binding relationship with the mobile terminal through message pushing by means of the application program after receiving the status message, which is sent by the first terminal and indicates the mood status of the first user. The pushing message is used to indicate the mood status of the user. When the another mobile terminal receives the pushing message, the user may be reminded of the mood status of the first user by means of a pop-up window through the locally-installed application program, such that the user who uses the another mobile terminal knows the mood status of the first user in time.

Besides, the mobile terminal may further send the pushing message that indicates the mood status of the second user to another mobile terminal through message pushing after determining the mood status of the second user who uses the mobile terminal. When the another mobile terminal receives the pushing message, the user may be reminded of the mood status of the second user, such that the user who uses the another mobile terminal knows the mood status of the second user in time.

To sum up, in the mood monitoring device provided by the embodiment of the present disclosure, the receiving module of the mood monitoring device receives the status message, which is sent by a terminal and indicates the mood status of the user. The control module may present a message that reflects the mood status of the user in accordance with the status message. For example, the light-emitting status parameter of the light-emitting unit is adjusted or the corresponding voice prompt is given. Compared with the prior art, the mood monitoring device provided by the embodiment of the present disclosure may help the user know the mood of another user, thus enhancing a mood exchange between relatives and friends in different places and improving the flexibility and reliability in mood monitoring.

Figure 5:
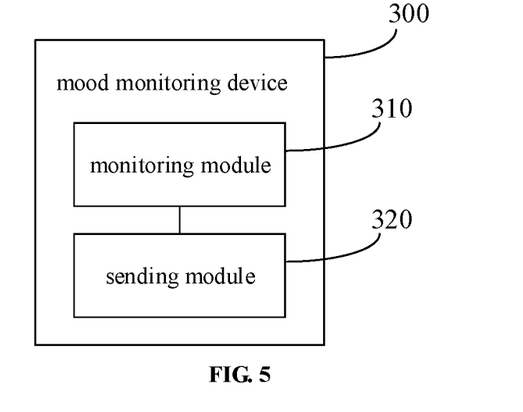
FIG. 5 is a structural diagram of another mood monitoring device provided in an embodiment of the present disclosure.

FIG. 5 illustrates a structural schematic view of a mood monitoring device provided by an embodiment of the present disclosure. The mood monitoring device may be applied to the first terminal 10 in the implementation environment shown in FIG. 1. Referring to FIG. 5, the mood monitoring device 300 comprises a monitoring module 310 and a sending module 320.

The monitoring module 310 is configured to monitor an EEG signal of a user, to determine a mood status of a user in accordance with the EEG signal and to generate a status message that indicates the mood status of the user.

The sending module 320 is configured to send the status message that indicates the mood status of the user to a terminal which has a binding relationship with the mood monitoring device. Exemplarily, the terminal may be the second terminal 20 in the implementation environment shown in FIG. 1. The user is the first user 30 who uses the first terminal 10. That is, the sending module of the first terminal is configured to send the status message that indicates the mood status of the first user to the second terminal.

Optionally, the sending module may be integrated with the monitoring module and may also be located outside the monitoring module to exist separately.

To sum up, in the mood monitoring device provided by the embodiment of the present disclosure, the monitoring module of the mood monitoring device monitors the EEG signal of the user, determines the mood status of the user in accordance with the monitored EEG signal and generates the status message that indicates the mood status of the user. The sending module sends the status message that indicates the mood status of the user to a terminal, such that the terminal may present a message that reflects the mood status of the user in accordance with the status message. Compared with the prior art, the mood monitoring device provided by the embodiment of the present disclosure may help the user know the mood of another user, thus enhancing a mood exchange between relatives and friends in different places and improving the flexibility and reliability in mood monitoring.

Figure 6:
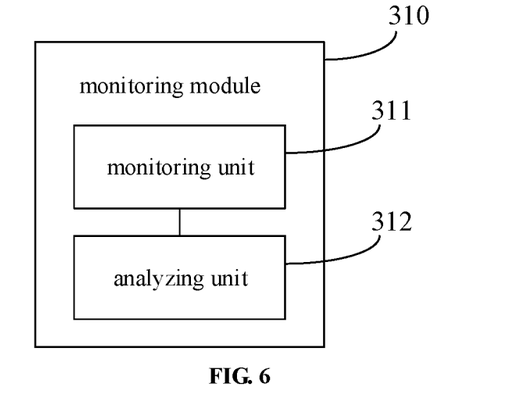
FIG. 6 is a structural diagram of a monitoring module provided in an embodiment of the present disclosure.

Optionally, as shown in FIG. 6, the monitoring module 310 may comprise a monitoring unit 311 and an analyzing unit 312. The analyzing unit may be integrated with the monitoring unit and may also be located outside the monitoring unit to exist separately. When the analyzing unit is located outside the monitoring unit, the monitoring unit 311 is configured to monitor an EEG signal of a user and to send the EEG signal to the analyzing unit 312. Exemplarily, the monitoring unit may be a portable EEG detector.

The analyzing unit 312 is configured to determine a mood status of the user in accordance with the EEG signal and to generate a status message that indicates the mood status of the user.

Exemplarily, the analyzing unit may be realized by an application program.

Optionally, the analyzing unit 312 is configured to acquire a frequency band of the EEG signal of the user, to inquire a corresponding relationship between a preset frequency band and the mood status, to acquire a target mood status that corresponds to the frequency band of the EEG signal of the user when the corresponding relationship has recorded the frequency band of the EEG signal of the user, and to determine the target mood status as the mood status of the user.

Exemplarily, the frequency band of the EEG signal of the user comprises a frequency band α, a frequency band A, a frequency band β and a frequency band B. Table 3 exemplarily illustrates two corresponding relationships between the mood status and the EEG signal. The mood status of the user is a relaxed status when the frequency band of the EEG signal of the user is the frequency band α or the frequency band A; and the mood status of the user is a tension status when the frequency band of the EEG signal of the user is the frequency band β or the frequency band B. Exemplarily, when acquiring that the frequency band of the EEG signal of the user is the frequency band α, the analyzing unit inquires Table 3 to acquire the target mood status (the relaxed status) that corresponds to the frequency band α. Then, the analyzing unit determines the relaxed status as the mood status of the user.

TABLE 3

| Frequency Band | Mood status |
| --- | --- |
| Frequency band α | Relaxed status |
| Frequency band A | Relaxed status |
| Frequency band β | Tension status |
| Frequency band B | Tension status |

Furthermore, the monitoring module 310 is further configured to provide a reference message in accordance with the mood status of the user. The reference message is used to prompt the user to adjust his/her mood status.

The monitoring module may count and analyze the mood status of the user within a preset period of time (for example, 5 days). The monitoring module may provide a reference message for the user to help the user adjust his/her mood status in time when monitoring that the mood status of the user is bad for physical and mental health of the user. For example, when the user is always depressed within a certain period of time or is depressed within a certain period of time every day recently, the first terminal may provide the reference message for the user via the monitoring module. The reference message may comprise a comedy movie message, a relaxation exercise message, a joke message, etc. The user may select an interesting message therefrom, for example, watch a comedy movie, to adjust his/her mood status, thus improving a physical condition.

Besides, mood status data of the user, counted by the monitoring module, may serve as reference data for follow-up seeking of a medical advice.

Likewise, the mood monitoring device may further comprise a receiving module and a control module. The receiving module is configured to receive a status message, which is sent by a terminal and indicates the mood status of the user. The control module is configured to present a message that reflects the mood status of the user in accordance with the status message. The user is the second user in the implementation environment shown in FIG. 1. The terminal is the second terminal in the implementation environment shown in FIG. 1. That is, the receiving module of the mood monitoring device may receive the status message, which is sent by the second terminal and indicates the mood status of the second user.

Optionally, the control module comprises a control unit and a light-emitting unit. The control unit is configured to adjust a light-emitting status parameter of the light-emitting unit in accordance with the status message that indicates the mood status of the user such that a light-emitting status of the light-emitting unit corresponds the mood status of the user. The light-emitting status parameter comprises at least one of a color, a brightness and a flash mode.

Optionally, the control unit is configured to inquire a corresponding relationship between a preset mood status and the light-emitting status parameter, to acquire a target light-emitting status parameter that corresponds to the mood status indicated by the status message when the corresponding relationship has recorded the mood status indicated by the status message, and to adjust the light-emitting status parameter of the light-emitting unit into the target light-emitting status parameter.

Optionally, the light-emitting unit comprises a red LED, a green LED and a blue LED. The control unit is configured to control the number and the current of light-emitting LEDs in each color in the light-emitting unit in accordance with the status message to adjust the light-emitting status parameter of the light-emitting unit.

Optionally, the control module further comprises a voice prompt unit. The control unit is further configured to control the voice prompt unit to give a voice prompt in accordance with the status message that indicates the mood status of the user such that the voice prompt corresponds to the mood status of the user. This process may refer to related description of the mood monitoring device shown in FIG. 2.

To sum up, in the mood monitoring device provided by the embodiment of the present disclosure, the monitoring module of the mood monitoring device monitors the EEG signal of the user, determines the mood status of the user in accordance with the monitored EEG signal, and generates the status message that indicates the mood status of the user. The sending module sends the status message that indicates the mood status of the user to a terminal, such that the terminal may present a message that reflects the mood status of the user in accordance with the status message. For example, the light-emitting status parameter of the light-emitting unit is adjusted or the corresponding voice prompt is given. Compared with the prior art, the mood monitoring device provided by the embodiment of the present disclosure may help the user know the mood of another user, thus enhancing a mood exchange between relatives and friends in different places and improving the flexibility and reliability in mood monitoring.

The embodiments of the present disclosure further provide a mood monitoring system, comprising a first terminal and a second terminal. Herein, the second terminal comprises the mood monitoring device shown in FIG. 2; and the first terminal comprises the mood monitoring device shown in FIG. 5.

To sum up, in the mood monitoring system provided by the embodiment of the present disclosure, the first terminal monitors the EEG signal of the user, determines the mood status of the user in accordance with the monitored EEG signal, and generates the status message that indicates the mood status of the user, and then sends the status message that indicates the mood status of the user to the second terminal, such that the second terminal may present a message that reflects the mood status of the user in accordance with the status message. For example, the light-emitting status parameter of the light-emitting unit is adjusted or the corresponding voice prompt is given. Compared with the related art, the mood monitoring system may help the user know the mood of another user, thus enhancing a mood exchange between relatives and friends in different places and improving the flexibility and reliability in mood monitoring.

Figure 7:
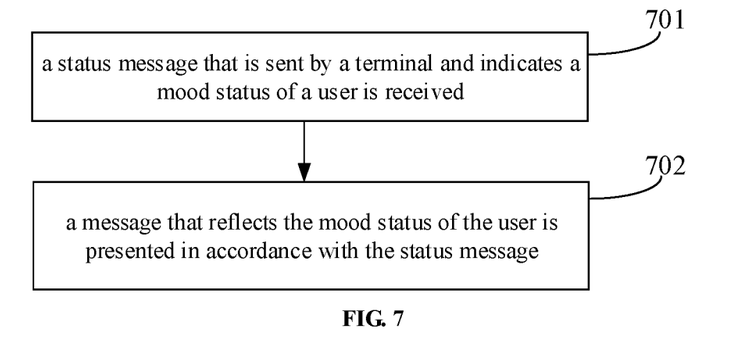
FIG. 7 is a flowchart of a mood monitoring method provided in an embodiment of the present disclosure.

The embodiments of the present disclosure further provide a mood monitoring method applied to the second terminal. As shown in FIG. 7, the method comprises the following steps.

In step 701, a status message that is sent by a terminal and indicates a mood status of a user is received.

Herein, the first terminal and the second terminal have a binding relationship. For example, the first terminal is the first terminal 10 in the implementation environment shown in FIG. 1, the second terminal is the second terminal 20 in the implementation environment shown in FIG. 1, and the user is the first user 30 using the first terminal 10.

In step 702, a message that reflects the mood status of the user is presented in accordance with the status message.

To sum up, with the mood monitoring method provided by the embodiment of the present disclosure, the second terminal receives the status message that is sent by the first terminal and indicates the mood status of the user, and presents a message that reflects the mood status of the user in accordance with the status message. Compared with the related art, the mood monitoring method may help the user know the mood of another user, thus enhancing a mood exchange between relatives and friends in different places and improving the flexibility and reliability in mood monitoring.

Figure 8:
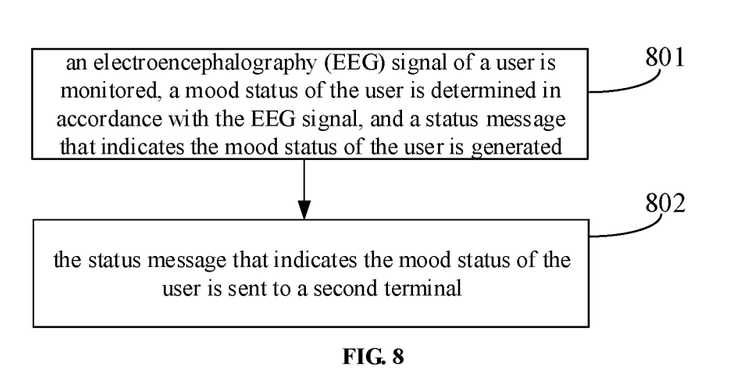
FIG. 8 is a flowchart of another mood monitoring method provided in an embodiment of the present disclosure.

The embodiments of the present disclosure further provide a mood monitoring method applied to the first terminal. As shown in FIG. 8, the method comprises the following steps.

In step 801, an electroencephalography (EEG) signal of a user is monitored, a mood status of the user is determined in accordance with the EEG signal, and a status message that indicates the mood status of the user is generated.

In step 802, the status message that indicates the mood status of the user is sent to a second terminal.

Herein, the second terminal and the first terminal have a binding relationship. For example, the first terminal is the first terminal 10 in the implementation environment shown in FIG. 1, the second terminal is the second terminal 20 in the implementation environment shown in FIG. 1, and the user is the first user 30 using the first terminal 10.

To sum up, with the mood monitoring method provided by the embodiment of the present disclosure, the first terminal monitors the electroencephalography (EEG) signal of the user, determines the mood status of the user in accordance with the EEG signal, and generates the status message that indicates the mood status of the user. Then, the first terminal sends the status message that indicates the mood status of the user to the second terminal such that the second terminal may present a message that reflects the mood status of the user in accordance with the status message. Compared with the related art, the mood monitoring method may help the user know the mood of another user, thus enhancing a mood exchange between relatives and friends in different places and improving the flexibility and reliability in mood monitoring.

Figure 9:
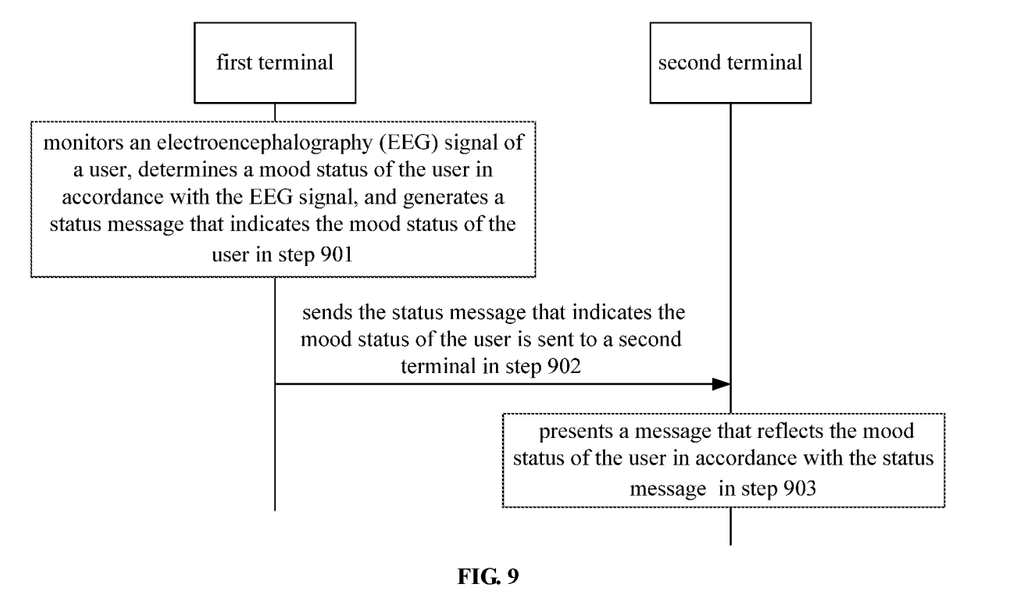
FIG. 9 is a flowchart of yet another mood monitoring method provided in an embodiment of the present disclosure.

The embodiments of the present disclosure further provide a mood monitoring method. As shown in FIG. 9, the method comprises the following steps.

In step 901, a first terminal monitors an electroencephalography (EEG) signal of a user, determines a mood status of the user in accordance with the EEG signal, and generates a status message that indicates the mood status of the user.

In step 902, the first terminal sends the status message that indicates the mood status of the user is sent to a second terminal.

Herein, the second terminal and the first terminal have a binding relationship. For example, the first terminal is the first terminal 10 in the implementation environment shown in FIG. 1, the second terminal is the second terminal 20 in the implementation environment shown in FIG. 1, and the user is the first user 30 using the first terminal 10.

In step 903, the second terminal presents a message that reflects the mood status of the user in accordance with the status message.

Figure 10:
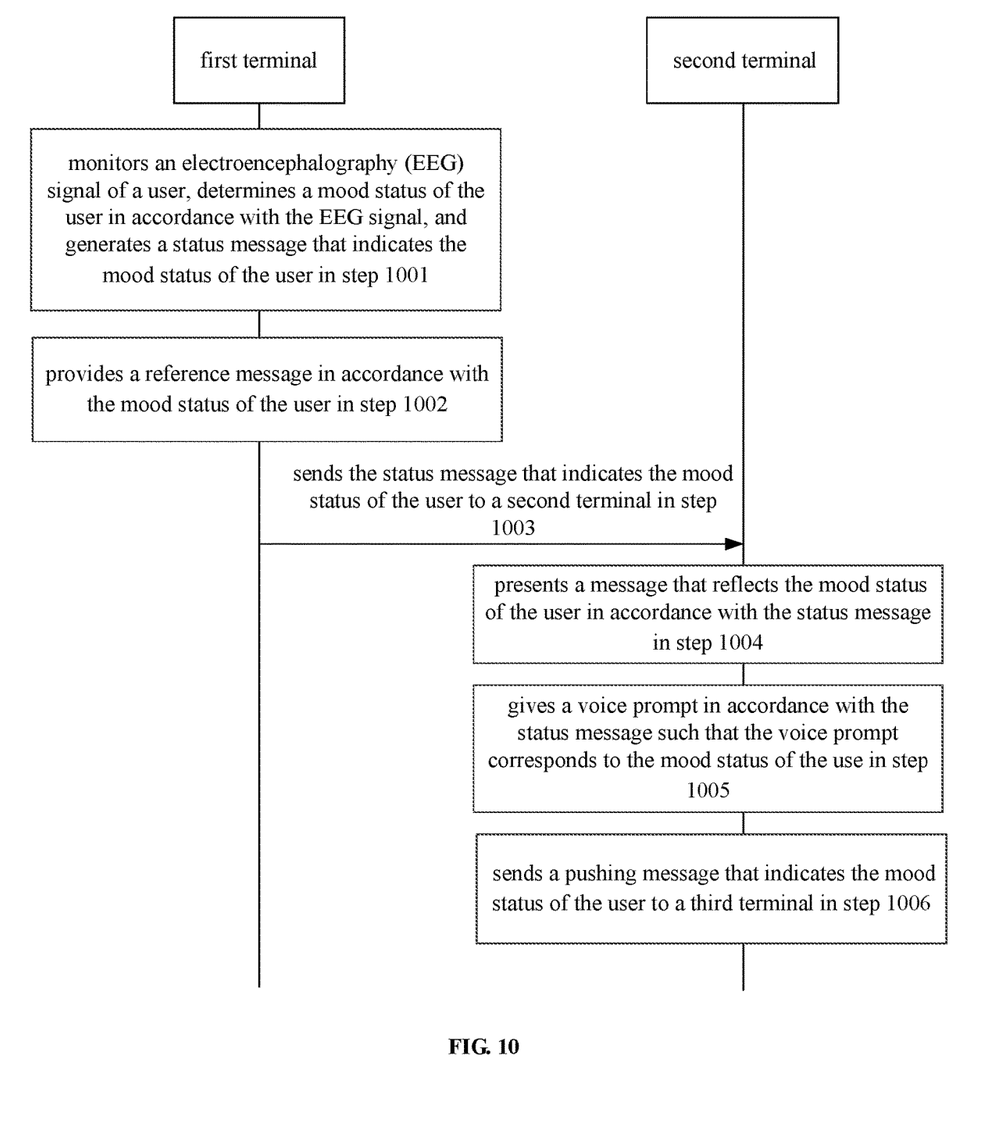
FIG. 10 is a flowchart of still yet another mood monitoring method provided in an embodiment of the present disclosure.

FIG. 10 is another mood monitoring method provided on the basis of FIG. 9 provided in an embodiment of the present disclosure. As shown in FIG. 10, the method may comprise the following steps.

In step 1001, a first terminal monitors an electroencephalography (EEG) signal of a user, determines a mood status of the user in accordance with the EEG signal, and generates a status message that indicates the mood status of the user.

Figure 11:
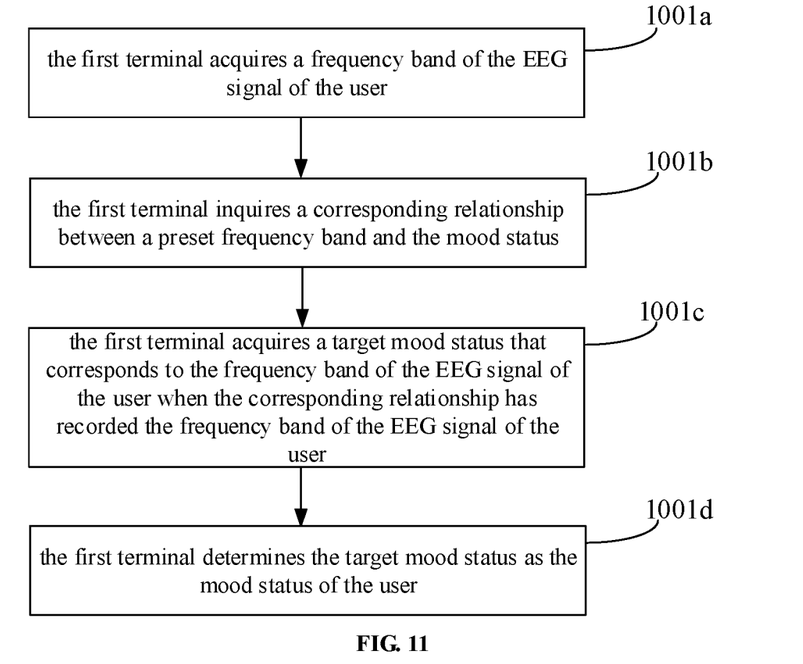
FIG. 11 is a flowchart of determining a mood status provided in an embodiment of the present disclosure.

Optionally, as shown in FIG. 11, monitoring an electroencephalography (EEG) signal of a user by the first terminal may comprise the following steps.

In step 1001a, the first terminal acquires a frequency band of the EEG signal of the user.

In step 1001b, the first terminal inquiries a corresponding relationship between a preset frequency band and the mood status.

In step 1001c, the first terminal acquires a target mood status that corresponds to the frequency band of the EEG signal of the user when the corresponding relationship has recorded the frequency band of the EEG signal of the user.

In step 1001d, the first terminal determines the target mood status as the mood status of the user.

In step 1002, the first terminal provides a reference message in accordance with the mood status of the user.

The reference message is used to prompt the user to adjust his/her mood status.

In step 1003, the first terminal sends the status message that indicates the mood status of the user to a second terminal.

Herein, the second terminal and the first terminal have a binding relationship. The first terminal is the first terminal 10 in the implementation environment shown in FIG. 1, the second terminal is the second terminal 20 in the implementation environment shown in FIG. 1, and the user is the first user 30 using the first terminal 10.

In step 1004, the second terminal presents a message that reflects the mood status of the user in accordance with the status message.

Optionally, the second terminal comprises a light-emitting diode (LED), and step 1004 may comprise the following steps: adjusting a light-emitting status parameter of the LED by means of the second terminal in accordance with the status message such that a light-emitting status of the LED corresponds to the mood status of the user, wherein the light-emitting status parameter comprises at least one of a color, a brightness and a flash mode.

Figure 12:
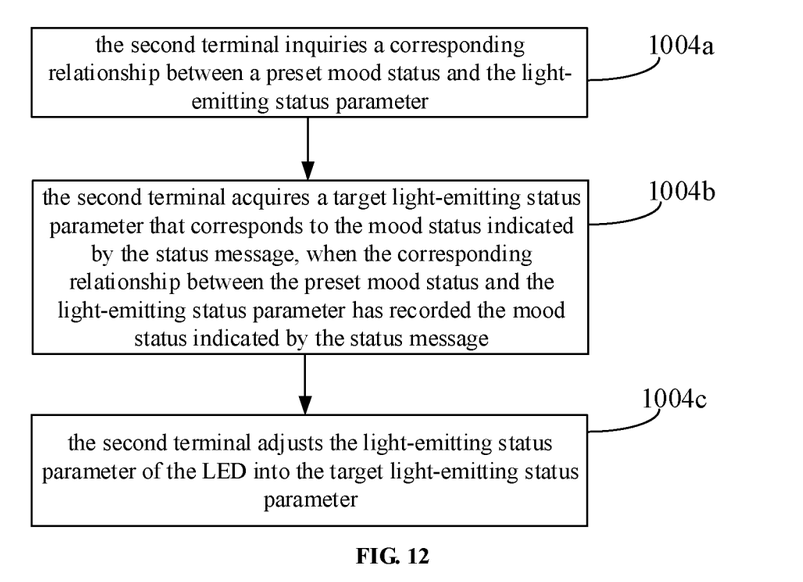
FIG. 12 is a flowchart of adjusting a light-emitting status parameter of a LED provided in an embodiment of the present disclosure.

As shown in FIG. 12, adjusting the light-emitting status parameter of the LED by means of the second terminal in accordance with the status message comprises the following steps.

In step 1004a, the second terminal inquiries a corresponding relationship between a preset mood status and the light-emitting status parameter.

In step 1004b, the second terminal acquires a target light-emitting status parameter that corresponds to the mood status indicated by the status message, when the corresponding relationship between the preset mood status and the light-emitting status parameter has recorded the mood status indicated by the status message.

In step 1004c, the second terminal adjusts the light-emitting status parameter of the LED into the target light-emitting status parameter.

Optionally, the LED comprises a red LED, a green LED and a blue LED. Corresponding, adjusting the light-emitting status parameter of the LED by means of the second terminal in accordance with the status message comprises: controlling the number and the current of light-emitting LEDs in each color in the LEDs by means of the second terminal in accordance with the status message to adjust the light-emitting status parameter of the LEDs.

In step 1005, the second terminal gives a voice prompt in accordance with the status message such that the voice prompt corresponds to the mood status of the user.

In step 1006, the second terminal sends a pushing message that indicates the mood status of the user to a third terminal.

Here, the third terminal has a binding relationship with the second terminal.

To sum up, with the mood monitoring method provided by the embodiment of the present disclosure, the first terminal monitors the electroencephalography (EEG) signal of the user, determines the mood status of the user in accordance with the EEG signal, and generates the status message that indicates the mood status of the user. Then, the first terminal sends the status message that indicates the mood status of the user to the second terminal such that the second terminal may present a message that reflects the mood status of the user in accordance with the status message. Compared with the related art, the mood monitoring method may help the user know the mood of another user, thus enhancing a mood exchange between relatives and friends in different places and improving the flexibility and reliability in mood monitoring.

The embodiments of the present disclosure further provide a mood monitoring device applied to the second terminal. The device comprises: one or a plurality of processors; and a storage, wherein the storage stores one or a plurality of programs, which is configured to be executed by the one or plurality of processors to implement the mood monitoring methods implemented by the second terminal in the above embodiments.

The embodiments of the present disclosure further provide a mood monitoring device applied to the second terminal. The device comprises: one or a plurality of processors; and a storage, wherein the storage stores one or a plurality of programs, which is configured to be executed by the one or plurality of processors to implement the mood monitoring methods implemented by the first terminal in the above embodiments.

The embodiments of the present disclosure further provide a non-volatile computer-readable storage medium including instructions stored therein. The computer-readable storage medium, when operating in a computer, causes the computer to implement the mood monitoring methods implemented by the second terminal above.

The embodiments of the present disclosure further provide a computer program product. The computer program product, when operating in a computer, causes the computer to implement the mood monitoring methods implemented by the second terminal above.

The embodiments of the present disclosure further provide a chip including programmable logic device and/or program instructions. The chip, when operating, is configured to implement the mood monitoring methods implemented by the second terminal above.

The embodiments of the present disclosure further provide a non-volatile computer-readable storage medium including instructions stored therein. The computer-readable storage medium, when operating in a computer, causes the computer to implement the mood monitoring methods implemented by the first terminal above.

The embodiments of the present disclosure further provide a computer program product. The computer program product, when operating in a computer, causes the computer to implement the mood monitoring methods implemented by the first terminal above.

The embodiments of the present disclosure further provide a chip including programmable logic device and/or program instructions. The chip, when operating, is configured to implement the mood monitoring methods implemented by the first terminal above.

It should be noted that the order of the steps in the mood monitoring method provided in the embodiments of the present disclosure may be adjusted appropriately, and the steps may be added or deleted according to circumstances. Any variation of the methods that may be easily derived by a person of ordinary skill in the art within the technical scope disclosed here shall fall within the protection scope of the present disclosure, which is not repeated here.

Persons of skills in the art may clearly understand that, for the convenience and conciseness of description, the procedures in the method embodiments described may be referred to the specific working procedures of the foregoing devices, modules and units, which are not repeated here.

The foregoing is only exemplary embodiments of the present disclosure, and are not intended to limit the present disclosure. Within the spirit and principles of the disclosure, any modifications, equivalent substitutions, improvements, etc., are within the scope of protection of the present disclosure.

What is claimed is:

1. A mood monitoring device, comprising:
one or a plurality of processors;
a storage; and
a light-emitting diode (LED), wherein
the storage stores one or a plurality of programs, which are configured to be executed by the one or plurality of processors and comprises instructions for performing the following operations:
receiving a status message that is sent by a terminal and indicates a mood status of a first user, the terminal and the mood monitoring device having a binding relationship and being located in different places; and
presenting a message that reflects the mood status of the first user in accordance with the status message, by adjusting a light-emitting status parameter of the LED in accordance with the status message such that a light-emitting status of the LED corresponds to the mood status of the first user, wherein the light-emitting status parameter comprises at least one of a color, a brightness and a flash mode, and the light-emitting status parameter corresponding to the mood status of the first user is set by a second user at the mood monitoring device in advance.

2. The mood monitoring device according to claim 1, wherein the one or plurality of programs further comprises instructions for performing the following operations:
inquiring a corresponding relationship between a preset mood status and the light-emitting status parameter;
acquiring a target light-emitting status parameter that corresponds to the mood status indicated by the status message when the corresponding relationship has recorded the mood status indicated by the status message; and
adjusting the light-emitting status parameter of the LED into the target light-emitting status parameter.

3. The mood monitoring device according to claim 1, wherein the LED comprises a red LED, a green LED and a blue LED, and
the one or plurality of programs further comprises instructions for performing the following operation:
controlling the number and the current of light-emitting LEDs in each color in the LEDs in accordance with the status message to adjust the light-emitting status parameter of the LEDs.

4. The mood monitoring device according to claim 1, wherein the one or plurality of programs further comprises instructions for performing the following operation:
giving a voice prompt in accordance with the status message such that the voice prompt corresponds to the mood status of the first user.

5. The mood monitoring device according to claim 1, wherein the one or plurality of programs further comprises instructions for performing the following operation:
sending a pushing message that indicates the mood status of the first user to another terminal which has a binding relationship with the mood monitoring device.

6. The mood monitoring device according to claim 1, being a mobile terminal.

7. A mood monitoring system, comprising a first terminal and a second terminal having a binding relationship with each other and being located in different places,
wherein the first terminal comprises:
one or a plurality of processors; and
a storage, wherein
the storage stores one or a plurality of programs, which is configured to be executed by the one or plurality of processors and comprises instructions for performing the following operations:
monitoring an electroencephalography (EEG) signal of a first user, determining a mood status of the first user in accordance with the EEG signal, and generating a status message that indicates the mood status of the first user; and
sending the status message that indicates the mood status of the first user to the second terminal, and
the second terminal comprises:
one or a plurality of processors;
a storage; and
a light-emitting diode (LED), wherein
the storage stores one or a plurality of programs, which are configured to be executed by the one or plurality of processors and comprises instructions for performing the following operations:
receiving the status message that is sent by the first terminal; and presenting a message that reflects the mood status of the first user in accordance with the status message, by adjusting a light-emitting status parameter of the LED in accordance with the status message such that a light-emitting status of the LED corresponds to the mood status of the first user, wherein the light-emitting status parameter comprises at least one of a color, a brightness and a flash mode, and the light-emitting status parameter corresponding to the mood status of the first user is set by a second user at the second terminal in advance.

8. The mood monitoring system according to claim 7, wherein the one or plurality of programs of the first terminal further comprises instructions for performing the following operations:
acquiring a frequency band of the EEG signal of the first user;
inquiring a corresponding relationship between a preset frequency band and the mood status;
acquiring a target mood status that corresponds to the frequency band of the EEG signal of the first user when the corresponding relationship has recorded the frequency band of the EEG signal of the first user; and
determining the target mood status as the mood status of the first user.

9. The mood monitoring system according to claim 7, wherein the one or plurality of programs of the first terminal further comprises instructions for performing the following operation:
providing a reference message in accordance with the mood status of the first user, the reference message being used to prompt the first user to adjust his/her mood status.

10. The mood monitoring system according to claim 7, wherein the first terminal is a mobile terminal.

11. The mood monitoring system according to claim 7, wherein the one or plurality of programs in the second terminal further comprises instructions for performing the following operations:
inquiring a corresponding relationship between a preset mood status and the light-emitting status parameter;
acquiring a target light-emitting status parameter that corresponds to the mood status indicated by the status message when the corresponding relationship has recorded the mood status indicated by the status message; and
adjusting the light-emitting status parameter of the LED into the target light-emitting status parameter.

12. The mood monitoring system according to claim 7, wherein the one or plurality of programs in the second terminal further comprises instructions for performing the following operation:
giving a voice prompt in accordance with the status message such that the voice prompt corresponds to the mood status of the first user.

13. The mood monitoring system according to claim 7, wherein the one or plurality of programs in the second terminal further comprises instructions for performing the following operation:
sending a pushing message that indicates the mood status of the first user to another terminal which has a binding relationship with the mood monitoring device.

14. A mood monitoring method, comprising steps of:
monitoring an electroencephalography (EEG) signal of a first user, determining a mood status of the first user in accordance with the EEG signal, and generating a status message that indicates the mood status of the first user, by means of a first terminal;
sending the status message that indicates the mood status of the first user to a second terminal which has a binding relationship with the first terminal, by means of the first terminal and being located in different places;
receiving the status message that is sent by the first terminal, by means of the second terminal; and
presenting a message that reflects the mood status of the user in accordance with the status message, by adjusting a light-emitting status parameter of the LED in accordance with the status message such that a light-emitting status of the LED corresponds to the mood status of the first user, by means of the second terminal, wherein the light-emitting status parameter comprises at least one of a color, a brightness and a flash mode, and the light-emitting status parameter corresponding to the mood status of the first user is set by a second user at the second terminal in advance.

15. The mood monitoring method according to claim 14, wherein said step of determining the mood status of the first user in accordance with the EEG signal by means of the first terminal comprises:
acquiring a frequency band of the EEG signal of the first user by means of the first terminal;
inquiring a corresponding relationship between a preset frequency band and the mood status by means of the first terminal;
acquiring a target mood status that corresponds to the frequency band of the EEG signal of the first user by means of the first terminal when the corresponding relationship between the preset frequency band and the mood status has recorded the frequency band of the EEG signal of the first user; and
determining the target mood status as the mood status of the first user by means of the first terminal.

16. The mood monitoring method according to claim 14, after said step of determining the mood status of the first user in accordance with the EEG signal, further comprising:
providing a reference message by means of the first terminal in accordance with the mood status of the first user, the reference message being used to prompt the first user to adjust his/her mood status.

17. The mood monitoring method according to claim 14, wherein said step of adjusting the light-emitting status parameter of the LED by means of the second terminal in accordance with the status message comprises:
inquiring a corresponding relationship between a preset mood status and the light-emitting status parameter by means of the second terminal;
acquiring a target light-emitting status parameter that corresponds to the mood status indicated by the status message, by means of the second terminal when the corresponding relationship between the preset mood status and the light-emitting status parameter has recorded the mood status indicated by the status message; and
adjusting the light-emitting status parameter of the LED into the target light-emitting status parameter by means of the second terminal.

18. The mood monitoring method according to claim 14, wherein the LED comprises a red LED, a green LED and a blue LED, and
said step of adjusting the light-emitting status parameter of the LED by means of the second terminal in accordance with the status message comprises:

controlling the number and the current of light-emitting LEDs in each color in the LEDs by means of the second terminal in accordance with the status message to adjust the light-emitting status parameter of the LEDs.

19. The mood monitoring method according to claim 14, after said sending the status message that indicates the mood status of the first user to the second terminal by means of the first terminal, further comprising:

giving a voice prompt by means of the second terminal in accordance with the status message such that the voice prompt corresponds to the mood status of the first user.

20. The mood monitoring method according to claim 14, after said sending the status message that indicates the mood status of the first user to the second terminal by means of the first terminal, further comprising:

sending a pushing message that indicates the mood status of the first user to a third terminal which has a binding relationship with the second terminal, by means of the second terminal.

* * * * *